(12) United States Patent
Kereteš, Jr. et al.

(10) Patent No.: US 6,576,268 B2
(45) Date of Patent: Jun. 10, 2003

(54) BIOLOGICALLY ACTIVE FRACTION OF VEGETABLE MELANIN, PROCESS FOR ITS PRODUCTION AND ITS USE

(75) Inventors: Ján Kereteš, Jr., Považská Bystrica (SL); Ján Kereteš, Považská Bystrica (SL); Ljubov Andrejevna Venger, Považská Bystrica (SL)

(73) Assignees: Jan Kerestes, Jr., Povazska Bystrica (SL); Jan Kerestes, Povazska Bystrica (SL)

(*) Notice: Subject to any disclaimer, the term of this patent is extended or adjusted under 35 U.S.C. 154(b) by 0 days.

(21) Appl. No.: 09/781,544

(22) Filed: Feb. 12, 2001

(65) Prior Publication Data

US 2002/0041905 A1 Apr. 11, 2002

Related U.S. Application Data

(63) Continuation of application No. PCT/SK99/00013, filed on Aug. 10, 1999.

(30) Foreign Application Priority Data

Aug. 13, 1998 (SL) .............................. 1098-98

(51) Int. Cl.$^7$ .............................. A61K 35/78
(52) U.S. Cl. ........................................ 424/725
(58) Field of Search ................ 424/725; 426/228, 426/541; 252/384; 514/2

(56) References Cited

U.S. PATENT DOCUMENTS 5,538,752 A * 7/1996 Blanchette et al.

FOREIGN PATENT DOCUMENTS

EP 0692480 * 5/1995
RU 2060818 C * 5/1996

OTHER PUBLICATIONS

Roberts, E.A.H., et al., J Sci Food Agric (1959); 10: 167–72. Phenolic substances of manufactured tea IV. Enzymic oxidations of individual substrates.*

* cited by examiner

Primary Examiner—Christopher R. Tate
Assistant Examiner—Michele C. Flood
(74) Attorney, Agent, or Firm—Pennie & Edmonds LLP

(57) ABSTRACT

A fraction of vegetable melanin, consisting of monomeric units of vegetable flavonoids, especially of catechins and leucoanthocyanidins, having a summary empirical formula of the H-form $[C_{34-59}O_{14-23}H_{32-44}N_{6-8}]_n$, where n=6 to 8, molecular weight $(5\pm1).10^3$ Da, the amount of —OH groups 4.02 to 4.05% by weight, the amount of =O groups 1.04 to 1.06% by weight, the content of individual elements (% by weight) C 49.44 to 49.52; H 5.10 to 5.73; N 1.15 to 1.24; O 41.20 to 42.10; concentration of unpaired electrons (spin/g) $10^{18}$ to $10^{22}$ and bright spectral lines in the regions 3433, 1620, 1400 and 1200 to 1100 cm$^{-1}$. A Process for production of vegetable melanin consists in that a vegetable raw material which contains native polymer and/or basic building units, such as catechins and lecoantocyanidines, is treated with 0.05 to 0.3 M aqueous solution of an alkali metal hydroxide at a temperature of 15 to 75° C., pH of the extract is adjusted to 1 to 2 by adding an inorganic acid, based on chlorine, wherein the excluded sediment is purified and subsequently dried at 100 to 110° C.

15 Claims, 1 Drawing Sheet

BIOLOGICALLY ACTIVE FRACTION OF VEGETABLE MELANIN, PROCESS FOR ITS PRODUCTION AND ITS USE

CROSS REFERENCE TO RELATED APPLICATION

This application is continuation of the U.S. national phase designation of International Application No. PCT/SK99/00013 filed on Aug. 10, 1999, the content of which is expressly incorporated herein by reference thereto.

TECHNICAL FIELD

The invention relates to melanins, suitable to be used in food industry, pharmacy, medicine and bioelectronics.

The invention relates also to a process for production of a narrow molecular fraction of melanin from raw materials of vegetable origin, so called phytomelanin, which exhibits defined and reproducible physico-chemical properties and higher biological activity than that of known, described vegetable melanins, and which is suitable to be practically used in industry and pharmacology.

BACKGROUND ART

Melanins—a general name for groups of high-molecular black and brown pigments, arising in the course of oxidation and polymerisation of phenols. Melanins occur normally in nature, and they are one of the most often occurring zoochromes. They occur in hair, eyes, skin, inner organs and so they are essentially mostly localised in the surface parts of organisms. Coloration of dark seeds, berries, flower leaves, and plants, men suntan, skin of blacks, many kinds of animals is mostly due melanins, as mentioned, for example, in Nicolaus R. A.: Melanins, Hermann, Paris 1968, p. 310; Lyiach S. P., Ruban R. D.: Mikrobnyie melaniny, Nauka, Moscow 1972, p. 184; and Bidzilja N. I.: Svobodnyie radikaly v oblutschennykh rastenyiach i semenakh, Naukova dumka, Kiev 1972, p. 210. The term "melanin" itself originates from a Greek word, and it means "black". Melanins are unique biopolymers which exhibit in a living organism protection function against UV radiation, ionising radiation, high and low temperatures. Melaninogenesis has been at present often presented as a complex adaptation of living organisms at the border of adaptability of life. It is possible to find unique examples of resistance of living organisms to geophysical and geochemical factors in extreme situations. These include first of all upland regions, where blackpigmented fungi constitute the only microflora at 4 to 5 km height, and also hot sandy and cold stony deserts of several regions [Lyiach S. P.: Mikrobnyi melaninogenez i yiego funktsii, Nauka, Moscow 1981, p. 274.; Ostrovskayia M., Dontsov A.: Fyziologitcheskyie funktsii melanina v organizme, Fyziologyia tscheloveka 1985, p. 670–679]. There are also organisms known which are stable when irradiated with sublethal doses of the order of 900 Krad. Inertness to γ-radiation decreases with the pigment loss, too. The question of melanin function in paleobiologicali aspect is extremely interesting. Highly melanised fungi spores occur in great amounts unusually often in the layers of the beginning of at "Cretaceous period" when many species of animals and plants died out. This period is identical with the period of the Earth's crossing the "magnetic zero", and thus of its inability to protect itself against cosmic radiation [Bidzilja N. I.: Svobodnyie radikaly v oblutschennykh rastenyiach i semenakh, Naukova dumka, Kiev 1972, p.210; Lyiach S. P.: Mikrobnyi melaninogenez i yiego funktsii, Nauka, Moscow 1981, p. 274; Ostrovskayia M., Dontsov A.: Fyziologitcheskyie funktsii melanina v organizme, Fyziologyia tscheloveka 1985, p. 670–679]. Hence, also a scientifically proven basis exists that melanins were the "beneficial" material which helped chemical evolution of some of polymeric prebiological structures. The above given possibility follows from the character of the process of synthesis of these substances, and from the properties of contemporary melanins. Great attention should be paid to the easiness with which are the pigments synthesized, when conditions are modelled which are supposed to have existed on the Earth in the period of origin of complicated substances from aromatic structures [Blois M. S.: Proischozhdenyie predbiologitscheskikh sistem, Mir, Moscow 1966, p. 494; Pavlovskayia T. E.: Abiogenez i natschalnyie stadii evolutsii zhizni, Nauka, Moscow 1968, p. 216; Blois M. S.: The melanins, their synthesis and structure, Photochem. and Photobiol. Rev. 3, 151, 1978: Swan G. A.: Current knowledge of melanin structure, Pigment cell, Vol.1, Harger, Basel 1973, p. 151].

Classification of Melanins

Depending on the biological subjects which synthesise them, melanins are divided in three basic groups: microbial, animal and vegetable. There exist also synthetic melanins which arise by autooxidation of 3,4-dihydroxydiphenylalanine (DOPA-melanin), as indicated, for example, by Mason H. S. in Pigment Cell Growth, Acad. Press, NY 1953, p. 235; Peers E.: Hystochemistry, IL, Moscow 1962, p. 640; Keretz D., Ann. intab. dermatol. din. esperimentele 1961, p. 268; and Thomas M.: Modern methods of plant analysis, Springer Verlag 1953, 4, p. 661. Microbial melanins are met only at some microorganisms, especially those belonging to the genera: Bacillus, Pseudomonas and Azatobaster (Azotobacter). These are black and brown, sometimes red-brown pigments which are, in general, insoluble in organic solvents, soluble in bases with non-specific spectral characteristics. Many facts prove that oxidation processes are the base for the origin of bacterial melanins. Attention should be paid to the fact that an absolute majority of microorganisms which synthesise the pigments, belong to aerobic forms. The animal melanins are localised in surface tissues—skin, hair, animal hair, feathers and retina. The vegetable melanins have been described only rarely. It is known that they occur in surface tissues of some seeds and fruits. Up to now three methods of vegetable melanins isolation are known and described, namely of the phytomelanin from Vitis Vinifera L. Nevertheless, the preparations are summary products showing broad spectrum of physico-chemical properties and, consequently, the product cannot be used as a drug base, as indicated in Zherebin J. L. et al.: Sposob polutschenyia vodorostvorimogo melanina, t. A. S. SSSR patent Nr. 939446, 1983; Sendega R. V., Venger L. A., Baklanova L. V.: Sposob polutschenyia enomelanina, patent A. S. SSSR Nr. 1345606, 1987; and Godzenko A. I. et al.: Sposob polutschenyia enomelanina, patent RU 07 09 93, bl. Nr. 33–36. The best described and known among the melanins is the so called synthetic melanin or DOPA-melanin which arises by autooxidation of 3,4-dihydroxydiphenylalanine (DOPA). The DOPA oxidation is going on in such a way and through such stages like the fermentative autooxidation of tyrosine in living organisms which results in the rise of animal and microbial melanins. A scheme of the process is given in Villee Claude A., Dethier Vincent G.: Biological principles and processes, Philadelphia-London-Toronto 1971, p. 822; and Brechtlová, Halča, Chandoga et al.: Lekárska biochémia I. (Medicinal biochemistry I), Asklepios 1992, p. 228.

3

Scheme:

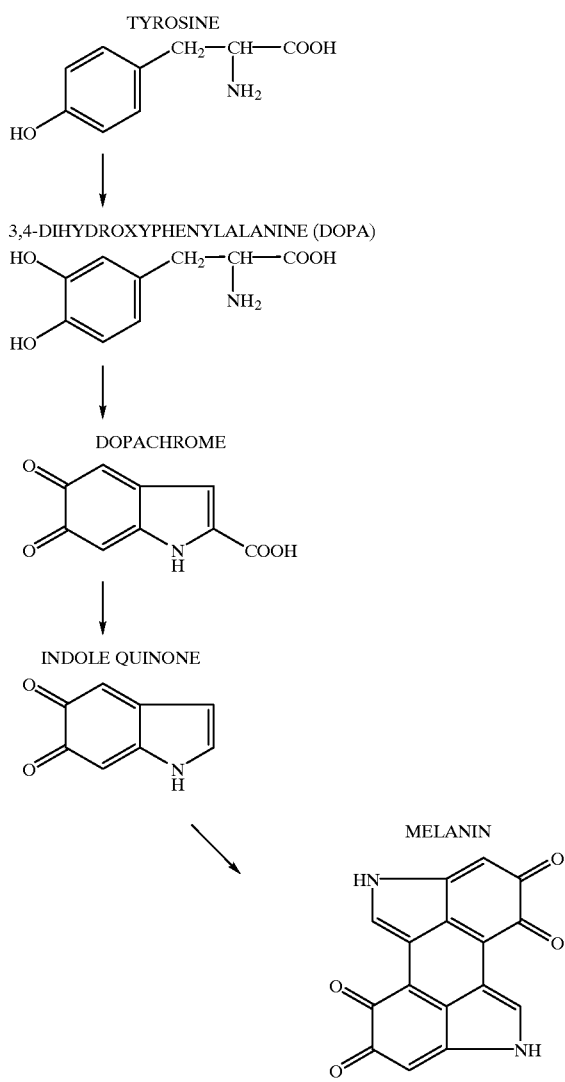

Chemical Structure and Melaninogenesis

Chemical structure of natural melanins has not been established yet, because they have very complicated polymeric structure and type diversity. Therefore, we could not obtain exhaustive description even for those pigments which have been investigated for several years. At present no unanimous opinion exists on the problem which compounds correspond to the term "melanin". Mason describes melanins as high-molecular polymers which arise in the course of enzymatic oxidation of phenols, especially of pyrocatechol, 3,4-dihydroxyphenylalanine, (DOPA) and 5,6-dihydroxyindole [Mason H. S. in Pigment Cell Growth, Acad. Press Inc., NY 1953, p. 235].

(Ia)

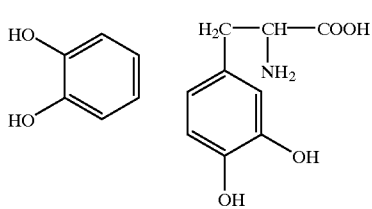

4

-continued

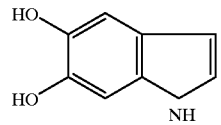

A related essay has been written by Nicolaus: "Natural melanins are complicated macromolecules which arise in the course of enzymatic oxidation of ortho-diphenols, mostly unsubstituted, such as 5,6-dihydroxyindole, pyrocatechinole and 1,8-dihydroxynaphthalene" [Nicolaus R. A.: Melanins, Hermann, Paris 1968, p. 310].

(Ib)

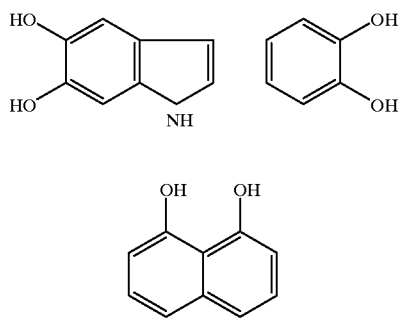

Peers and Keretz describe melanin pigments arising in the course of oxidation of aromatic amino acids: tyrosine and dihydroxyphenylalanine [Peers E.: Hystochemistry, IL, Moscow 1962, p. 640; Keretz D., Ann. intab. dermatol. din. esperimentele 1961, p. 268]. Thomas proposes to consider as melanins only nitrogen containing pigments, i.e. derivatives of 5,6-dihydroxyindole which occurs either in an oxidised or in a reduced state [Thomas M.: Modern methods of plant analysis, Springer Verlag 1953, 4, p. 661].

At present two basic theories on the origin and structure of zumelanins exist. The first states that zumelanins are essentially homopolymers of indole-5,6-quinone [Pulman B., Pulman A.: Kvantovayia biokhimyia, Mir, Moscow 1965, p. 654]. The second, Nicolaus's interpretation, results from many experiments performed assuming that in the mechanism of melanogenesis free radical polymerisation of various monomers takes place. The polyfunctionality of monomers, the absence of precise bond structure between the radicals lead to the synthesis of polymers having non-uniform content and organisation structure. This finally lead to the opinion that in nature there probably do not exist any two absolutely identical melanin pigments [Nicolaus R. A.: Melanins, Hermann, Paris 1968, p. 310]. Therefore, melanin is a three-dimensional polymer for which the number of possible structures is equal to the number of types of melanin molecules in nature. For many years the pigment of the Ustilago maydis fungus spores has been considered as the basic model. It is practically the only (microbial) mela nin the structure of which has been, in general, examined and confirmed (Formula IIa).

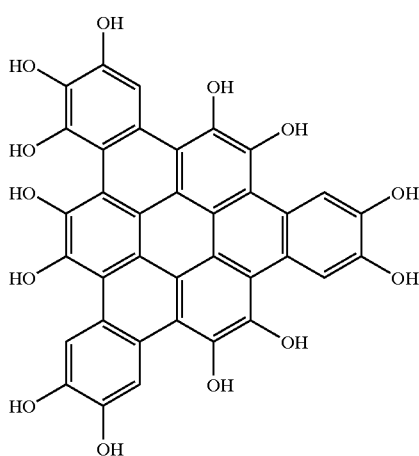

(IIa)

Nicolaus concludes that complicated cyclic structures with condensed rings, occurring in different oxidation states, arise in the course of polymerisation of pyrocatechinole to melanin [Nicolaus R. A.: Melanins, Hermann, Paris 1968, p.310; Lyiach S. P., Ruban R. D.: Mikrobnyie melaniny, Nauka, Moscow 1972, p.184].

The second, essentially examined melanin is the black pigment arising in ripe spores of the *Aspergillus niger* fungus. It belongs to the group of so called alomelanins, and it is called *Aspergillus niger*-melanin [Nicolaus R. A.: Melanins, Hermann, Paris 1968, p.310; Blois M. S.: Prois-chozhdenyie predbiologitscheskich sistem, Mir, Moscow 1966, p.464].

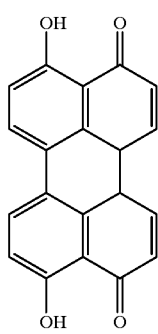

(IIb)

At present it is possible to assume that the base for melaninogenesis in living organisms consists in a process which is based on fermentative oxidation of tyrosine via DOPA in the presence of tyrosinase to dopaquinone of which pigment arises through a number of oxidations, decarboxylations and conjugations. This is the "classical way".

Anyway, the synthesis sometimes passes a different path and the melanogen may be not only tyrosine, but also other phenols, for example pyrocatechinole. In spite of that it should be remembered that the genetically conditioned ability to form tyrosinase and melanin pigments in living organisms is highly stable on the whole [Brechtlová, Halčik, Chandoga et al.: Lekárska biochémia I (Medicinal biochemistry 1), Asklepios 1992, p. 228; Škárka B., Ferenčik M.: Biochémia, Alfa, Bratislava 1992, p. 846].

Identification of Melanins

One of the reasons for insufficient examination of melanins is the problem of their isolation from biological objects, because these pigments are insoluble in most of known organic and mineral solvents [Nicolaus R. A.: Melanins, Hermann, Paris 1968, p. 310; Lyiach S. P.: Mikrobnyi melaninogenez i yiego funktsii, Nauka, Moscow 1981, p. 274; Blois M. S.: The melanins, their synthesis and structure, Photochem. and Photobiol. Rev. 3, 151, 1978]. Moreover, melanin is present in biological objects in vivo, and it readily binds to other polymers: proteins, polysaccharides, lipids, other pigments and admixtures.

Difficulties with and problems of isolation of melanins consist also in their colloid character and inability to crystallise. As a consequence two basic methods of melanin pigments isolation exist.

The first group of methods consists in melanin extraction with suitable solvents, and then in elimination of accompanying admixtures. The only, nearly universal solvents for melanins are 0.5 to 1.0 M aqueous solutions of the bases NaOH and KOH. Such properties of melanins are conditioned by their polyphenolic structure. Therefore, also alkaline extraction is used for isolation of melanins from cells and tissues of animals, microbial and some vegetable subjects.

The second group of melanin extraction methods is presented as a method in which all other materials except melanin are eliminated. This elimination of useless materials is performed by hydrolysis with an acid and washing with suitable solvent until the required preparation—melanin—remains [Lyiach S. P., Ruban R. D.: Mikrobnyie melaniny, Nauka, Moscow 1972, p. 184].

As a consequence, no standard method, suitable for all kinds of natural melanins, can be proposed and described, because chemical complexity and diversity of biological materials and specialities of melanins alone require individual approach. For example, for the extraction of ustilago-melanin another Process for preparative technique is used. Spores of the Ustilago maydis fungus are treated by concentrated HCl and then, using various solvents, admixtures are removed. Melanins of some subjects are essentially easily isolated by "soft methods". This concerns, for example, melanin of bull's eye iris or melanin of the ink of the octopus *Sepia officinalis*—sepiomelanin. The preparations are isolated without treating with an acid or a base, because they occur in the biological subject in the form of sodium salts. But there are only very few such examples. In principle, the method of alkaline extraction with the following precipitation by an acid is used for melanins of animal, microbial and vegetable origin [Nicolaus R. A.: Melanins, Hermann, Paris 1968, p.310].

The melanin content in the cells of fungi is varying in a broad range: from 2 to 3% by weight up to 35 to 40%. The melanin content in vegetable subjects is considerably lower, namely from 0.2 to 0.3% by weight up to 6 to 8% by weight.

One of the identification tests for melanins are the VIS spectra. Melanins exhibit bright spectral absorption lines, one in the wavelength region of 1600 to 1700 $cm^{-1}$, the second in the region of 3000 to 3500 $cm^{-1}$. The spectral lines correspond to carbonyl groups (absorption in the region of 1700 $cm^{-1}$), carbon-carbon bonds (absorption in the region of 1600 $cm^{-1}$), $NH_4$ and OH-groups (absorption in the region of 3300 to 3500 $cm^{-1}$).

Melanins of natural, as well as of synthetic origin show a characteristic UV-spectrum in which they show neither any peaks nor clear absorption bands, especially in the range of short wavelengths. A similar characteristics is in the region of visible part of the spectra with an inclined diagonal within the limits of −0.0019 to −0.0040. Such optical characteristics are typical for melanins.

Also various chemical reactions are characteristic, by which it is possible to judge whether the melanin monomers occur in the preparation:

a/ insolubility in water and in most organic solvents, b/ full solubility in 0.5 M NaOH or KOH, c/ precipitation from solutions in the presence of $FeCl_3$, d/ discoloration if strong oxidation agents ($KMnO_4$, $H_2O_2$) are used, e/ ability to regenerate ammonia solution of $AgNO_3$.

The most important characteristics of melanin pigments is the presence of paramagnetic centres with a concentration of $10^{15}$ to $10^{18}$ spin/g [Nicolaus R. A.: Melanins, Hermann, Paris 1968, p. 310; Bidzilja N. I.: Svobodnyie radikaly v oblutschennykh rastenyiach i semenakh, Naukova dumka, Kiev 1972, p. 210; Ostrovskayia M., Dontsov A.: Fysiologitscheskyie funktsii melanina v organizme, Fyziologyia tscheloveka 1985, p. 670–679].

From the biological point of view determination of the melanin nature of pigments consists in the isolation of tyrosinase and of its substrates in the subjects given, and also determination of direct connection between tyrosinase activity and melaninogenesis (pigmentogenesis).

Therefore, identification of melanin based on one or two tests is not unequivocal, so that a whole complex of tests must be used. The presence of an unoccupied bottom energy level in melanins and their ability to "trap" unpaired electrons from the environment leads to the fact that melanin exhibits radioprotective properties absorbing unpaired electrons of free radicals, arising in the systems under the action of ionising radiation [Bidzilja N. I.: Svobodnyie radikaly v oblutschennykh rastenyiach i semenakh, Naukova dumka, Kiev 1972, p. 210; Godzenko A. I. et al.: Sposob polutschenyia enomelanina, patent RU 07 09 93, bl. Nr. 33–36].

In the last years results of experimental studies have been published which have confirmed the radioprotective properties of melanins. Melenins exhibit the properties when naturally occurring in the subject, but also when they are artificially introduced into a living organism [Hill H. Z., Hill G. J.: Eumelanin Causes DNA Strand Breaks and Kills Cells, Pigments Cell Research 1, 163–170, 1987; Hill H. Z., Peak J. G., Peak M. J.: Induction of DNA-protein crosslinks in melanotic cloudman S91 mouse melanoma cells by monochromatic 254 and 405 nm light, Pigment Cell Research 2, 427–430, 1989; Tsuneaki Chida, Hugh D. Sisler: Effect of inhibitors of melanin biosynthesis on appresorial penetration and reductive reactions in *Pyricularia oryzae* and *Pyricularia grisea*, Pesticide Biochemistry and Physiology 29, 244–251, 1987; Jacobsohn M. K., Dobre V. C., Branam Ch., Jacobsohn G. M.: Oxidation of 2-hydroxyestradiol and its incorporation into melanin by mushroom tyrosinase, J. Steroid Biochem. 31(4A), 377–385, 1988; Giovanni Sichel: Biosynthesis and function of melanins in hepatic pigmentary system, Pigment Cell Research 1, 250–258, 1988]. The experiments which have been performed on black cells containing melanin of the yeast *Nadsomiela nigra* have shown that these are considerably more resistant to radiation than the cells of yeasts which contain no melanins. By artificial cultivating of yeasts in biological medium, containing hexachloroacetone which is an inhibitor of melaninogenesis, a culture has been cultivated which has completely lost resistance against radiation [Chrulyiova I. M.: lssledovanyie struktury i svoystv melanina i yego syntetitscheskikh analogov, Ref. Zh., Moscow 1973, p. 20; Baraboyi V. A.: Biologitscheskoyie deystvyie rastitelnykh fenolnykh soyiedinenyi, Naukova dumka, Kiev 1976, p. 260; Zherebin J. L. et al.: Farmakologitscheskyie svoystva enomelaninovykh pigmentov, Doklady AN SSSR, seryia B 1984, pp. 64–68].

The results of practical experiments and review of the literature available make it possible to develop a melanin preparation which would serve as an effective radioprotector for living cells of organisms, produced on the basis of natural materials and products of metabolism.

Antitumour Activity of Melanin Pigments

At present most of research workers and scientists believe that a cancer cell differs from a normal cell not by the fact that it lacks some specific substances, but by the ratio of components of biochemical systems, belonging to a normal cell. The works of N. M. Emanuel et al. have confirmed that a change of concentration of free radicals in biochemical components of the cell is essential for negative growth of the cell and, therefore, antioxidants must influence the progress of the processes. Based on this, the authors could assume that such physico-chemical property of melanins like antioxidation activity is an important indicator of the process of the cell metabolism. It is a basis for the ability of phenol groups to react with free radicals—active centres of the cell biochemical system. An elementary act of co-operation of an inhibitor with a free radical R leads in the system to creation of an inhibitor radical which is more stable and less reactive than the radical R [Chrulyiova I. M.: Issledovanyie struktury i svoystv melanina i yego syntetitscheskikh analogov, Ref., Moscow 1973, p. 20].

This hypothesis has been confirmed in scientific studies. At that time synthetic, natural (animal) and biosynthetic melanins were chosen as a subject for the investigation. The animal melanin was obtained from the mice melanoma Harding-Passa by an acidic-alkaline method. The biosynthetic melanin was synthesized from DOPA in the presence of tyrosinase, isolated from the mice melanoma Harding-Passa [Chrulyiova I. M., Berlin A. A.: Protivoopukholyievayia aktivnost syntetitscheskikh, biosyntetitscheskikh i prirodnykh melaninov, Izvestiya AN SSSR 1973, Nr. 3, pp. 438–442]. Based on the performed experiments it could be proven that melanins are not carcinogenic, and the results allowed to confirm that melanins have the ability to show antitumour activity with doses of 150 to 250 mg/kg, reaching the effect of 50 to 60% retardation of the tumour growth.

Immunogenic Activity of Melanin Pigments

At present such great amount of medicinal preparations exists, as never before. As a rule, after some time papers appear in the literature stating an increased sensibility to a new preparation. There were many measures accepted and experiments performed to establish any dependence between the physico-chemical properties and immunogenic activity [Vladimirov V. G., Krasilmikov I. J., Arapov O. B.: Radioprotektory, Naukova dumka, Liev 1980, p. 264; VIDAL cat.—Lekarstvennyie preparaty v Rossii, Astra-Pharm-Servis, Moscow 1997, p. 1166] of medicinal compounds for the purpose of foreseeing and judging their allergicity. To date it is not possible to perform such corrections because of the level of present scientific knowledge. Nevertheless, several facts have been established which may be presented as follows. Immunogenic activity of an antigen depends on its physico-chemical properties and on the ability of the immunising (immunised) organism to response to a given antigen. According to the ability to elicit an immune response the antigens may be classified into two groups—weak and strong. Among the substances with established chemical nature the strongest immunogens are proteins, although also polysaccharides, synthetic polypeptides and other polymers may become immunogens under certain conditions [Koen S., Word P., Mat-Classen R.: Immunology, Medicina, Moscow 1983, p. 400; Allergeny i immunopatologyia v klinike i experimente, Sbornik nautschnykh trudov, Moscow 1988, p. 164; Buc M. et al.: Klinická imunológia, Veda, Bratislava 1997, p. 364]. Sufficiently high molecular weight is also a condition for sufficient immunogenecity of antigens. For example, if the molecular weight is less than 10 000, as a rule the substance is weakly immunogenic.

Most of the high-molecular proteins have the molecular weight over 100 000. With decreasing dimensions and molecular weight of antigens individuality of their structure is getting lost, heterogeneity and immunogenic activity decrease. It has been observed that the more complicated is the structure of the molecule of an antigen the more immunogenic it is. An example has been shown in the case of immunogenecity of synthetic polypeptides. If the polypeptide was formed of residues of one amino acid, it was weakly immunogenic. If it consisted of more kinds of residues of two or three amino acids, it gained immunogenic properties. The presence of aromatic amino acids (for example tyrosine) in synthetic polypeptides ensures immunogenicity of the molecule. It has been shown that the ability to elicit creation of antibodies at high levels belongs to substances which have groups, charged at their surface.

Some theories connect the immune activity of compounds also with the strength of their molecule. From this point of view immunogenicity, the ability to induce the cell or humoral immune response, depends on individuality and physico-chemical properties of the antigen, on dimensions of its molecule, on the character, amount and localisation of antigenic determinants in the antigen molecule.

Based on the above given facts and other general knowledge on the properties of animal, microbial, vegetable and synthetic melanins all these substances have the property of immunogenic activity, and presumably they may be classified into the group of weak antigens.

Pharmacological Properties of Melanins

When using melanins for pharmacological reasons, their solubility is of great importance. In the studies, described up to now, melanin preparations have been used in the form of aqueous suspensions or suspensions in physiological saline, they have been applied intramuscularly, but they were practically never absorbed and, therefore, they have had only local effects. The most effective are soluble melanins which are applied perorally or intravenously. Similar preparations have been produced, but they consisted mostly of pseudoglobulin melanoproteins, i.e. complexes of chromogenic parts with proteins which are not able to transport electrons and have a reduced ability to protect against the influence of radiation and toxic free radicals [Buc M. et al.: Klinická imunológia, Veda, Bratislava 1997, p. 364; Ferenčik M., Štvrtinová V., Bernadič M., Jakubovský J., Hulín I.: Zápal, horúčka, bolest', Slovak Academic Press, Bratislava 1997, p. 216; Mayer V., Hallauer J., Baum M. K.: Ochorenie, spôsobené náikazou virusom HIV/AIDS, Vydavatel'stvo Slovenskej akadémie vied, Bratislava 1996, p. 364].

There is concern in the investigation of pharmacological activity of water-soluble (chromogenic) part of the pigment, extracted from vegetable cultures—fytomelanin.

Melanin Preparations in the World

At present, especially in the period of the last 15 years, more and more attention is concentrated on melanins as perspective preparations for many areas in industry and medicine. Melanins are produced at present by a number of companies; the best known are the products, produced and distributed by SIGMA CHEMICAL Corp., USA [Sigma Chemical Co.: Biochemikalien und Reagenzien für die naturwissenschaftliche Forschung, Germany 1997, p. 2736; The Merck Index, An encyclopedia of chemicals, drugs and biologicals, 12$^{th}$ Edition, Whitehouse Station, N.Y. 1996, p. 2668].

Up to now production of synthetic melanin (so called DOPA-melanin) and sepiomelanin, isolated from the ink of Sepia officinalis, has been mastered. Nevertheless, because of exotic raw materials the preparations are very expensive, they are produced in insufficient amounts, and they are in general not available for broad usage. Small amounts of several kinds of melanins of animal and microbial origin are produced in laboratories, but because of high complexity of the production and because of lack of basic raw materials they do not represent serious and cheap possibilities of a large scale industrial production. Production of melanins of vegetable origin in chemically pure form is not known up to the present.

All known processes are based on the isolation of melanin by complicated method from biological structures in which they occur or on synthetic methods, i.e. on autooxidation of tyrosine.

Disclosure of the Invention

The above mentioned disadvantages are eliminated to a great extent by biologically active fraction of melanin according to this invention, the structure of which results from polymerisation of vegetable flavonoids, especially of catechins and lecoanto-cyanidines (III).

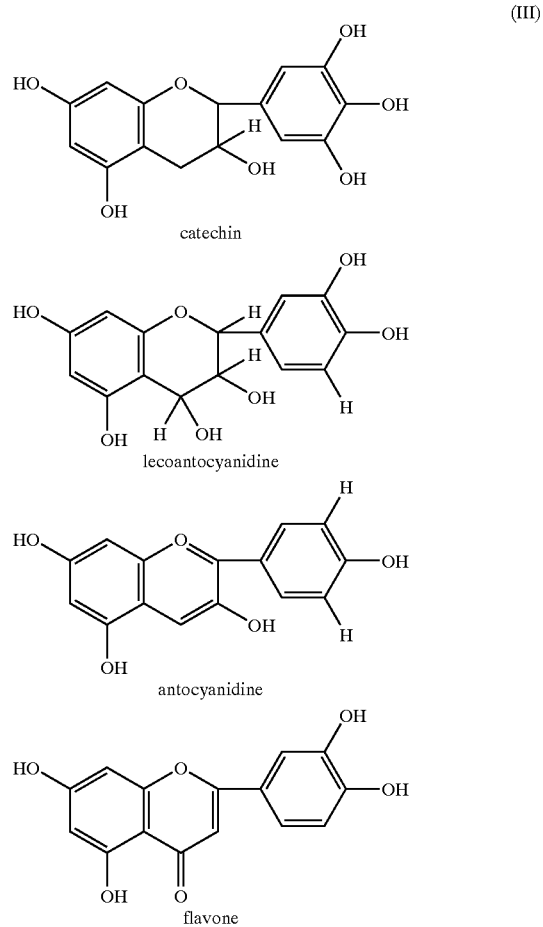

As the fraction of melanin is an amorphous substance, it is impossible to determine its precise structure. As an example we present one of the most probable structures (IV), where the arrows indicate further paths of possible polymerization.

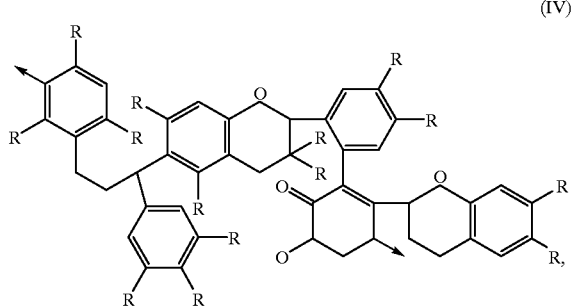

(IV)

where R is independently OH, H═O, —COOH or —NH$_2$.

The base for the fytomelanin molecule is a structure, consisting of monomeric units of vegetable flavonoids according to this invention, especially of catechins and lecoantocyanidines. As the polymerization itself and, therefore, the number of possibilities of forming different structures is rather high, the limiting factor here is the molecular weight Mh=(5±1).10$^3$ Da.

The empirical formula for one of the most probable structures which is represented by the formula IV is

[C$_{34-59}$O$_{14-23}$H$_{32-44}$N$_{6-8}$]$_n$, where n=6 to 8

In the next Table 1 there are given physico-chemical properties of the substance, arising as a result of polymerization of vegetable flavonoids according to the technology which we have proposed.

TABLE 1

| Physico-chemical properties of fytomelanin | |
|---|---|
| Molecular weight | (5 ± 1) · 10$^3$ Da |
| —OH groups | 4.02 to 4.05% by weight |
| ═O groups | 1.04 to 1.06% by weight |
| Content of individual elements (% by weight) | |
| C | 49.44 to 49.52 |
| H | 5.10 to 5.73 |
| N | 1.15 to 1.24 |
| O | 41.20 to 42.10 |
| Concentration of unpaired electrons (spin/g) | 10$^{18}$ to 10$^{22}$ |
| Spectrum (cm$^{-1}$) | 3433, 1620, 1400 1200 to 1100 |

"Melanins of vegetable origin" is just an overall summary name for dark brown and black pigments of plants which are, from the chemical point of view, products of oxidation of flavan-3,4-diols. Taking into account that the reaction of oxidation polymerization is influenced by a number of factors, such as temperature, pH of the environment, hydromodule, phase ratio, reaction time, content and concentration of components, and the like, also its products may partially differ and they have no strict physico-chemical characteristics or they also differ considerably one from the other.

The structure of melanins is the most probable structure if conditions for polymerization in the course of their synthesis from natural vegetable raw materials are provided as further described in detail, and if corresponding technological procedure is used. These conditions practically eliminate the way of condensation of flavonoids with opening the pyran cycle (the scheme after K. Freidenberg), but they correspond to the reaction according to the scheme after D. E. Katueno with joining molecules "head to head" and "tail to tail" [Kretovich V. A.: Osnovy biokhimii rastenyi, Vysschayia schkola 1970, p. 540].

Besides, the base of the molecule of known melanins is pyrocatechinol structure (formula II) which arises as a result of the opening of the pyran cycle of the lekoantocyanidine molecules and by the following polymerization of the formed fragments. It can be explained by "harder" conditions, where one of the main reasons is the usage of high concentration of bases, 0.25 to 1.20 M, of nonadequate thermal modes, usage of non-demineralised water in the whole process or only partially. Moreover, the technology which we have proposed ensures that a structure of a polymer arises having not very high condensation degree (n=5 to 7), in consequence of what it is possible to synthesise chemically homogeneous product—a polymer, fytomelanin having certain physico-chemical and biological characteristics and reproducible properties.

Isolation of natural polymer from biological subjects is practically impossible. This refers especially to melanins of vegetable origin for which there exists no inert solvent. The only solvents are 0.5 to 1.0 M aqueous solutions of NaOH or KOH. Nevertheless, the process of dissolution is not a physical process, but it is actually chemical reaction of a base with a polymer which causes destruction of the native biopolymer. This action severely disturbs the chemical nature, actually leading to decomposition to individual fragments which are further "sewn together" according to one of the known schemes of oxidation polymerization. By the subsequent procedure arising admixtures and other reaction products are eliminated.

The product prepared in this way is no more the original native form, but a synthetic polymer which is also characterised by the properties, belonging to the original melanins and to this class of compounds. In this respect we may, therefore, speak about a synthesis of the product in a biochemical way on the base of the original vegetable raw materials.

Identification

One of the tests for fytomelanin identification are the VIS-spectra. Bright spectral absorption bands:
  in the wavelength range of 1600 to 1700 cm$^{-1}$
  in the wavelength range of 3300 to 3500 cm$^{-1}$.

The spectral bands correspond to carbonyl groups (absorption in the range of 1700 cm$^{-1}$), carbon-carbon bonds (absorption in the range of 1600 cm$^{-1}$), NH$_4$ and OH— groups (absorption in the range of 3300 to 3500 cm$^{-1}$) (Table 1).

The further identification features or characteristics are as follows:
  a/ insolubility in water and in most organic solvents
  b/ complete solubility in 0.5 M NaOH or KOH,
  c/ precipitation from solutions in the presence of FeCl$_3$,
  d/ discoloration if strong oxidation agents (KMnO$_4$, H$_2$O$_2$) are used,
  e/ ability to regenerate ammonia solution of AgNO$_3$.

The most important characteristics of the fytomelanin is the presence of paramagnetic centres (unpaired free electrons) with a concentration of 10$^{18}$ to 10$^{22}$ spin/g.

The Process for production of a fraction of vegetable melanin consists in that the vegetable raw material is treated with a 0.05 to 0.3 M aqueous solution of an alkali metal hydroxide at a temperature of 15 to 75° C., pH of the extract is adjusted to 1 to 2 by adding an inorganic acid, based on chlorine, and the excluded sediment is purified and subsequently dried at 100 to 110° C.

The purification is preferably performed by washing with a solution of an acid, based on chlorine, having pH of 1.0 to 3, until colourless liquid is reached over the sediment, by subsequent washing with ethanol and with further organic polar solvents. In all of the processes water of pharmacological quality is used.

The dry product may be further subjected to further purification, and semiquinonic radical is activated.

The Process for preparation of a substance the physico-chemical parameters of which correspond to Table 1, consists in the following steps:

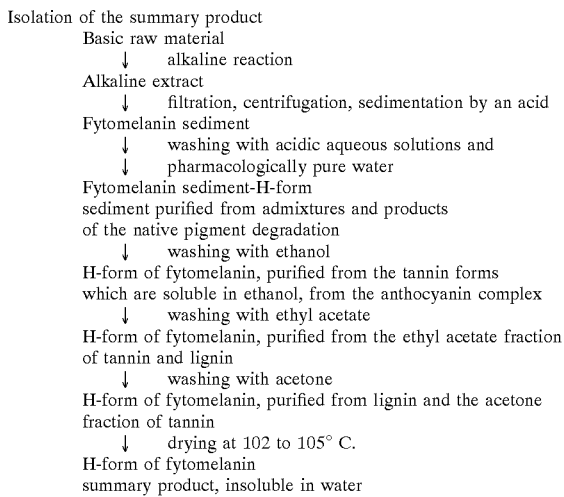

The obtained summary product represents a fraction of vegetable melanins, having a molecular weight $Mh=(5\pm2) \cdot 10^3$ Da. A further stage of the technological process is removing of the residual accompanying admixtures and products of the native polymer degradation.

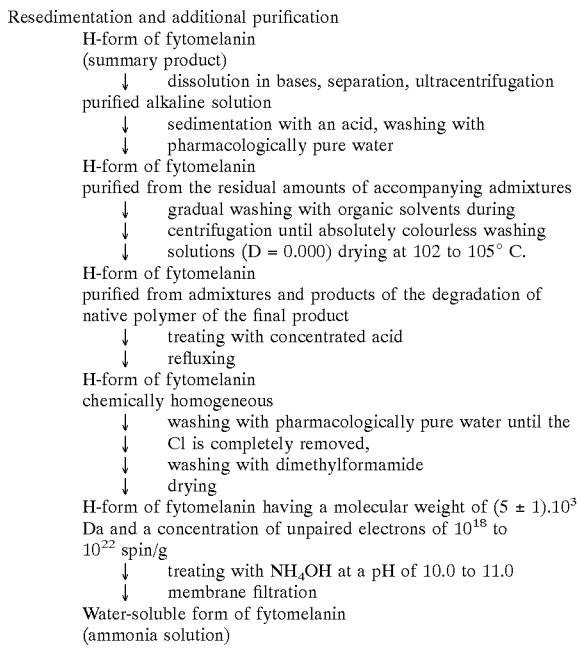

The final product may be prepared in the following forms:
a) dry amorphous powder with dark brown colour, showing characteristic metallic lustre, insoluble in water
b) dry amorphous powder with dark brown colour, showing characteristic metallic lustre, soluble in water
c) aqueous solution of fytomelanin with maximum concentration up to 3 to 5% by weight
d) paste with dark brown colour, containing 10 to 15% by weight of the basic product.

The nature of the invention consists also in a pharmaceutical preparation which contains a fraction of the vegetable melanin according to this invention and a pharmaceutically acceptable carrier.

It was found that a fraction of the vegetable melanin according to this invention is suitable to be used as a drug, especially as an antioxidant, to block the peroxidation of lipids, to activate leukocytes, to regulate the behaviour of the complement system. Based on the results achieved which are described below and on the description of biological functions of substances having melanin character [Ferenčik M., Štvrtinová V., Bernadič M., Jakubovský J., Hulín I.: Zápal, horúčka, bolesť, Slovak Academic Press, Bratislava 1997 ,p 216; Mayer V., Hallauer J., Baum M. K.: Ochorenie, spôsobené nákazou vírusom HIV/AIDS, Vydavateľstvo Slovenskej akadémie vied, Bratislava 1996, p. 364; Sigma Chemical Co.: Biochemikalien und Reagenzien für die naturwissenschaftliche Forschung, Germany 1997, p. 2736; Ďuračková Z., Bergendi L'., Liptáková A., Muchová J.: Free radicals derived from oxygen and medicine, Bratislava Medical Journal 1993, Nr. 8, 419–434; Ďuračková Z., Felix K., Feniková L', Kepštová I., Labuda J., West U.: Superoxide dismutase mimetic activity of a cyclic tetrameric Schiff base N-coordinated Cu(II) complex, BioMetals, Nr. 5, 183–187, 1995; Novák M.: Neuroimmunology of the Alzheimer's Disease, Bratislava Medical journal 1997, 98, 303–314] we can conclude the following:

A damage in a human organism arises through the action of external or inner factors. It should be understood that the term "damage" includes measurable changes at which homeostasis of the intracellular environment is damaged to such a degree that the intracellular structures and the cells themselves are not able to hold and compensate the disorder by their own mechanisms. At this moment a disorder of subcellular structures and loss of cell integrity encounters. If the process affects a sufficiently high number of cells the irreversible cell conditions manifest themselves by the loss of the corresponding organ function. It results in a disorder of organs with subsequent changes of functions of the whole organism.

Melanins, including fytomelanin, belong to a group of substances which take part in the corrective measures. It means that it is not a substance which compensates the loss or disorder in any way. Neither is it a substance which would act as a factor of deficiency supplementation. It is a substance which actively affects the processes which start when homeostasis of cells and subsequently of the whole organs is damaged. In accordance with modern concepts of medicine the solution of the problem of cell and organ damages is a principal solution. This approach observes the modern trends in the development of scientific research in the field of biological-medical sciences. The principle of cell homeostasis loss is the basis for all disorders in the human organism except for genetically conditioned disorders. Also the action of physical factors such as radiation, action of extreme temperatures and physical factors causes disorder of the cell structure. The organism must also in these cases ensure optimisation of conditions in the sense of organism survival. That what happens in the organism subsequently, is a process in which many mechanisms and substances take part. The substance fytomelanin plays crucial role in the process. It follows from the fact that in the damaging process mechanisms are activated which are directed to elimination of the damaging injurer. At the same time substances arise which have high bactericide activity and the ability to react very rapidly with other substances which occur in the place of damage. The substances directed to elimination of the injurer have no ability to recognise the damage of useful and useless parts of the organism. As a final consequence these substances damage all structures occurring at the place of their rise, forming and action. In most cases these are substances with small molecular weight. A similar process of damaging takes place also if a disorder encounters of an organ or tissue which has already been damaged and adapted. For example in the case of atherosclerosis a certain kind of equilibrium state arises between a disordered vessel, blood flow and the tissue which is supplied with blood from the vessel. If the cell integrity is disturbed (preatherosclerotic process), again mechanisms directed to remedy and organism survival start to act in this dramatic situation. These and the above mentioned processes of damage remedy take place with forming reactive oxygen intermediates, superoxide anion, hydrogen peroxide, hydroxyl radical, singlet oxygen and reactive nitrogen intermediates. Based on the present analyses, fytomelanin works as a means for the "control" of forming these substances. These substances are able to react with the injurer, but their important role consists in that they trigger a cascade of changes of forming other substances which act as damaging substances and as substances which ensure activation and regulation of the remedy processes. Exchange of intercell information is influenced by these substances. The substances, used for treatment so far, have a character of substances with attenuating or stimulating effect. Other substances have a function of supplementation or competitive inhibition.

Fytomelanin is a substance the effect of which depends on the activation state in the case of damage and on the activation state of the systems taking part in these complex processes (complement system, coagulation system and kinin system). Fytomelanin works really as a regulator which might serve for the complete control of processes which take place spontaneously. For the preparation of a research concept concerning an overall utilisation in medicine directed to elucidation of the role of this molecular fraction of melanins of vegetable origin it is further necessary to perform observations of a model situation on an integral organism (reperfusion damages, oxygen and calcium paradox). These would be studies which should define the participation of fytomelanin in damage and remedy of an organism. Fytomelanin—substance may by especially perspective, its binding to enzymes and to substances, containing metal elements, may result in very broad utilisation. Moreover, a substance which behaves as a process regulator might be useful if used in many lethal diseases and in the elucidation of the origin of many diseases which are not yet explained.

The fytomelanin fraction according to the present invention, as an active substance to be used as a drug, may be used in the following pharmacological forms: water-soluble dry form, injection form, dry substance for peroral administration, solution for injection application, solution for peroral administration, tablets, granules, capsules, dragée, suspensions, syrup, gel, jelly, ointment, creams, solution for external application, solution for infusions, aerosol forms, cosmetic additive for liquids, creams, shampoos.

BRIEF DESCRIPTION OF THE DRAWING

In the attached drawing is shown a calibration curve used when measuring antioxidant ability of fytomelanin.

EXAMPLES

Example 1

Figure 1:
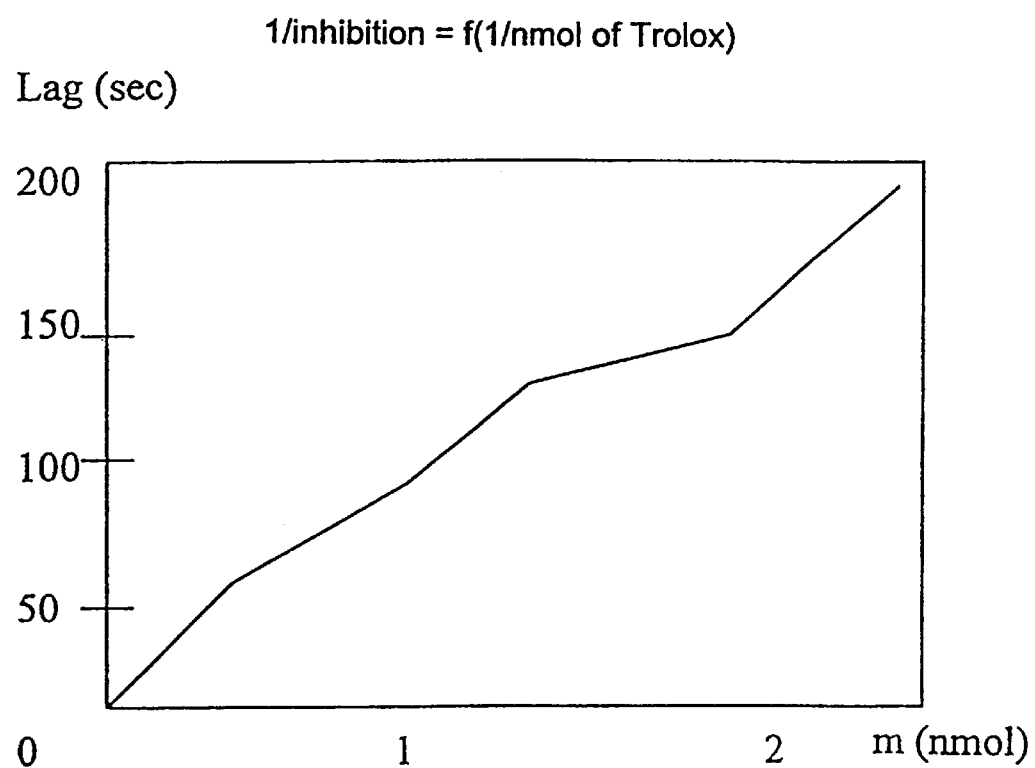

Process for Production of *Aesculus hippocastanicum* L.—fytomelanin

As a basic raw material for the product isolation hulls of *Aesculus hippocastanicum* were used in an amount of 2000 g which were separated from the kernels before, washed with water and dried to maximum of 10% by weight of water.

Chemical substances used:
demineralised water of pharmacological quality
    HCl 37% fuming p.a.
    NaOH p.a.
    ethanol p.a.
    ethylester of acetic acid p.a.
    acetone p.a.
    dimethylformamide p.a.

For sedimentation and washing any acid, based on chlorine, may be used, but, because of simplicity, the most preferred is the hydrochloric acid.

Equipment used:
    laboratory glass
    centrifuge Heraeus Megafuge 2
    vacuum evaporator Heidolph W 2000
demineralising station Nerner Ro6
    magnetic stirrer and accessories
    control and measuring equipment
    other devices and accessories (drying box, . . . )

Isolation of the Summary Product from *Aesculus hippocastanicum* L.

Basic Raw Material
- dried hulls were divided into 10 glass vessels each having the volume of 3500 ml; each vessel received 200 g of dried hulls of *Aesculus hippocastanicum*,
- on the prepared raw material 0.3 M solution of NaOH was poured, stirred for 30 min. and the whole mixture was heated to a temperature of 50° C. The reaction time was 10 hours.

Alkaline Extract
- after 10 hours the extract was purified from coarse mechanical admixtures on a coarse filter, and using the centrifuge with 3500 rev./min. small and microscopic mechanical impurities were removed
- 32 l of alkaline extract were obtained on the whole, and the extract was evenly distributed into 10 glass reaction bottles, each having the volume of 20 l
- each of the bottles was filled to the full volume by pharmacologically pure water, and it was completed with HCl to reach the pH value of 1.5
- the whole mixture was stirred and in a short time sediment has arisen having red-brown to dark brown colour which was left to sediment for 12 hours.

Sediment of the fytomelanin of *Aesculus hippocastanicum* L.
- the formed sediment was separated from the liquid component of the mixture in a centrifuge
- the sediment was further washed with a weakly acidic aqueous solution of HCl at a pH value of the medium pH 1.5 to 3.0 until the liquid over the sediment was colourless (10×repeated washing) at a mixture ratio of 1:8.

Sediment of the Fytomelanin of *Aesculus hippocastanicum* L.—H-form

- separated and concentrated sediment was further washed with ethanol, and it was separated from the liquid in the centrifuge
- washing with ethanol was continued while the ethanol was coloured with the admixtures which are soluble in ethanol
- it was further successively washed with ethyl acetate and subsequently with acetone until the state was achieved that the organic solvents were not coloured with the admixtures which are soluble in them
- the product was dried in air at a room temperature
- the dried product was ground in a laboratory mill to a grain size of 0.200 to 0.250 mm
- it was sieved through a laboratory sieve 0.25 mm
- it was dried at a temperature of 100 to 110° C. to constant weight.

H-form of the Fytomelanin of *Aesculus Hippocastanicum*
Summary Product Insoluble in Water
Dark Brown Powder with Metallic Lustre The obtained summary product represents a fraction of vegetable melanins with Mh=(5±2).10³ Da. The next stage of the technological process is removing the residual accompanying admixtures and products of native polymer degradation.

Resedimentation and Additional Purification
H-form of the Fytomelanin of *Aesculus Hippocastanicum* (Summary Product)

The obtained H-form was again dissolved in 20 l of 0.3 M NaOH, the obtained alkaline extract was centrifuged until microscopic mechanical impurities were completely removed. The centrifugation was performed at 3500 rev./minute for 25 minutes. The obtained purified extract was diluted with 5-fold amount of pharmacologically pure water, and HCl was added to pH 2.0. For the complete removing of admixtures it was sufficient to wash 3 times with aqueous solution of HCl at pH 2.0 to 3.0.

Successive washing with organic solvents was performed in the sequence ethanol, ethyl acetate, acetone, while centrifuging to absolutely colourless washing solutions (D=0.000). The product was dried at 102 to 105° C.

H-form of the fytomelanin *Aesculus hippocastanicum* was obtained, pure from admixtures and products of native polymer degradation, as a dark brown powder having a characteristic metallic lustre.

Final Product
H-form of the Fytomelanin *Aesculus Hippocastanicum*, Pure from Admixtures and Products of Native Polymer Degradation The obtained product was treated with 6 M HCl under reflux during 6 hours, mixture ratio 1:5. The product was washed with pharmacologically pure water until $Cl^-$ were completely removed which was confirmed by a qualitative reaction for $Cl^-$.

A product was obtained—H-form of fytomelanin, chemically homogeneous. To increase biological activity and activation of the semiquinonic radical the product was suspended with dimethylformamide 1:5, the suspension was separated by centrifugation at 2400 rev./min. for 10 minutes. The product was dried at 102 to 105° C. for 120 minutes.

To obtain the water-soluble form the preparation was dissolved in an aqueous solution of $NH_4OH$ which was prepared so that the pH value was 10 to 11, the excess ammonia was evaporated in a vacuum evaporator, and a part of the solution was concentrated to 1.375% by weight.

Water-soluble form of fytomelanin, so called *Aesculus hippocastanicum*—melanin. The obtained product is a powder having dark brown to black colour which dissolves completely in redistilled (apirogenic) water, maximum concentration is about 5% by weight.

Properties of the preparation correspond to Table 1, concentration of unpaired electrons is $10^{19}$ spin/g.

Using this technology 17.565 g of the final product were produced from 2000 g of the raw material, i.e. 0.87% by weight, related to the total weight of the raw material.

Depending on the batch of hulls of *Aesculum hippocastanicum*, i.e. of the basic raw material, the number of washings and the amount of the reagents used may differ from the above given example within certain limits. Therefore, also the total amount of the final product may differ within the limits of 0.7 to 1.15%.

This fact and slight differences in technology and output of the final product are caused by the fact that natural raw materials in the actual case of *Aesculus hippocastanicum* L. do not have identical chemical composition and homogeneity, while some parts of them may even differ considerably, depending on the climatic conditions and on the trees (plants) themselves.

Examples 2 to 9

As a basic raw material for the fytomelanin production following starting products were used:

*Castanea sativa*
*Thea* L.
*Vitis vinifera* L.
*Fagopyrum esculentum* L.
*Heliantus annus* L.
*Hippophae ramnoides* L.
*Vicia faba* L.
*Junglas regia* L.

TABLE 2

Physico-chemical properties of vegetable fytomelanins

| N | Raw material | Mh Da × $10^3$ | —OH % by weight | =O % by weight | Chemical composition element, % by weight | | | | EPR spin/g | $k_{abs}$ at $\lambda = 465$ nm |
|---|---|---|---|---|---|---|---|---|---|---|
| | | | | | C | H | N | O | | |
| 1 | *Vitis vinifera* | 5 ± 1 | 4.05 | 1.06 | 49.52 | 5.73 | 1.14 | 41.20 | $10^{18}$ | 0.019 |
| 2 | *F. esculentum* | 5 ± 1 | 4.08 | 1.03 | 49.63 | 5.84 | 1.20 | 41.49 | $10^{18}$ | 0.019 |

TABLE 2-continued

Physico-chemical properties of vegetable fytomelanins

| N | Raw material | Mh Da × $10^3$ | —OH % by weight | =O % by weight | Chemical composition element, % by weight | | | | EPR spin/g | $k_{abs}$ at λ = 46 5 nm |
|---|---|---|---|---|---|---|---|---|---|---|
| | | | | | C | H | N | O | | |
| 3 | Helianthus a. | 5 ± 1 | 4.04 | 1.00 | 49.58 | 5.46 | 1.32 | 41.66 | $10^{18}$ | 0.019 |
| 4 | Hippophae r. | 5 ± 1 | 4.08 | 1.02 | 49.20 | 5.04 | 1.40 | 42.36 | $10^{19}$ | 0.019 |
| 5 | Thea L. | 5 ± 1 | 4.00 | 1.04 | 49.12 | 5.08 | 1.28 | 42.68 | $10^{20}$ | 0.019 |
| 6 | Vicia faba L. | 5 ± 1 | 4.09 | 1.06 | 49.80 | 4.95 | 1.28 | 42.92 | $10^{18}$ | 0.019 |
| 7 | Junglas reg. | 5 ± 1 | 4.04 | 1.04 | 49.44 | 5.10 | 1.24 | 42.10 | 1019 | 0.019 |

Spectrum for all kinds ($cm^{-1}$): 3433, 1620, 1450, 1220–1100

These starting raw materials were processed in the same way as in Example 1. Properties of the fractions obtained from these raw materials fitted well with the properties given in Table 1. Investigations on given vegetable raw materials have shown that it is possible to produce—biosynthesize fytomelanin from all of the types, the final product is the same and does not depend on the type of the basic raw material. It is obvious from the tables and from the above cited literature that the probable content of fytomelanin in vegetable subjects is lower than the value which we have reached. It attests to the fact that non-polymerised monomeric units of vegetable flavonoids were polymerised by our technology to the final product—fytomelanin. Therefore, it is possible to produce fytomelanin also from a raw material which does not contain the original native polymer, but only monomers of the basic building units of the polymer—fytomelanin. We may speak in this case about synthesis of the product. On the basis of the above given facts we may assume that all other, up to now not investigated melanised plants (raw materials) also contain fytomelanin which may be obtained in the described form, while the difference consists only in slightly differing concentration of unpaired electrons (paramagnetic centres), depending on the degree of activation of the semiquinonic radical. The conclusion refers also to other kinds of raw materials which have a sufficient content of vegetable flavonoids suitable for fytomelanin polymerization.

To make the process of washing with weakly acidic aqueous solutions (HCl) more effective it is possible to use the solution heated up to a temperature of max. 75° C., the consequence of which is a lower number of washings.

Based on the results achieved and the conclusions derived we suppose that using the new methods of activation (electrochemical way, irradiation, washing, suspending with other suitable polar solvents and acids) of the semiquinonic radical we can reach the EPR value—concentration of unpaired free electrons of $10^{22}$ spin/g. At the same time, on the basis of practical results which will be given below we suppose that an increase of this value simultaneously increases biological activity of fytomelanin, and potentialises its possibilities and, therefore, also possibilities and eventual way of utilisation.

It is not always necessary to perform resedimentation if the starting product corresponds to the required quality after the first sedimentation already. This is caused by various kinds of the input raw materials and by their different quality. If we, for example, use as a raw material black fermented Vietnamese tea which has already been treated for direct usage, the input quality of the raw material is so high and the product so homogeneous that it is not necessary to use purification and resedimentation to achieve a final product, having properties corresponding to Table 1 and characterised by biological activity.

Pharmacological Properties of Fytomelanin

Based on toxicological tests performed it has been established that fytomelanin is non-toxic and it is not a mutagenic preparation. Its toxicity is very low, $LD_{50}$>2500 mg/kg, leading to the conclusion that the substance may be used as a fytopharmacon, based on preliminary results. As a standard for basic studies Aesculus hippocastanicum—melanin (hereinafter fytomelanin) was used. It was converted to the ammonia form and stored at a temperature of 8 to 10° C. during 3 months. Then the sample was used to determine experimentally its biological activity. The original sample which was used in the complex of biological activity testing showed the level of EPR $1.47.10^{18}$ spin/g. Next batch, used for comparison (SOD-like activity and $IC_{50}$), has shown the value of $2.8.10^{19}$ spin/g. The difference has arisen as a result of better chemical purification of the preparation and activation of the semiquinonic radical by repeated suspending in polar organic solvents.

Some of the antioxidant properties of fytomelanin were determined experimentally which may be summarised under certain assumptions and with explanation of basic terms.

Free radicals are highly reactive molecules, derived from oxygen or nitrogen, which play, apart from a positive role in some physiological processes, predominantly negative role. Against the toxicity of free radicals there exist in the organism or, in general, in nature substances which are able to eliminate them. The substances are generally designated as antioxidants [Brechtlová, Halčák, Chandoga et al.: Lekárska biochémia I, Asklepios 1992, p. 228; Duračkova Z., Bergendi L', Liptáková A., Muchová J.: Free radicals derived from oxygen and medicine, Bratislava Medical Journal 1993, Nr. 8, 419–434; Ďuračková Z., Felix K., Feniková L', Kepštová I., Labuda J., West U.: Superoxide dismutase mimetic activity of a cyclic tetrameric Schiff base N-coordinated Cu(II) complex, BioMetals, Nr. 5, 183–187, 1995].

By a series of practical experiments, based on the present modern and established methods, some basic antioxidant properties were determined which confirmed perspectivity and broad possibilities of utilisation in this field. Antioxidant properties of this substance, fytomelanin with EPR of the order of $10^{18}$ spin/g, were determined.

Determination of an Overall Antioxidant Ability (Total Antioxidant Status)

To determine the total antioxidant status the set TAS from Randox, Great Britain, was used. The method is based on the creation of the radical Abts$^+$ (2,2'-azino-di-(3-ethylbenzthiazoline sulphonate)). The radical arises as a result of the action of hydrogen peroxide on metmyoglobin, where ferrylmyoglobin arises which reacts with Abts under creation of the Abts$^+$ radical.

$$HX\text{---}Fe^{3+} + H_2O_2 \longrightarrow X\text{---}(Fe^{4+}=O) + H_2O$$

$$Abts + X\text{---}(Fe^{4+}=O) \longrightarrow Abts^+ + HX\text{---}Fe^{3+}$$

$$HX\text{---}Fe^{3+} \qquad \text{metmyoglobin}$$

$$X\text{---}(Fe^{4+}=O) \qquad \text{ferrylmyoglobin}$$

Samples were prepared and pipetted according to the procedure given in the set. Results of the antioxidant ability of the substance are expressed by the concentration of Trolox which was used as a standard for the calculation of the antioxidant activity. We have subtracted the blank absorbance from the measured absorbancies, and calculated the Trolox-like concentration in the sample according to the formula:

$$C_{vz} = \frac{(A_{BL} - A_{VZ})}{(A_{bl} - A_{st})} \times C_{ST}$$

The results are given in the following Table 3:

TABLE 3

| fytomelanin [c] | Trolox-like [c] | Trolox-like [c]/ LX [c] |
|---|---|---|
| 0.1 | 0.663 | 6.63 |
| 0.01 | 0.113 | 11.29 |
| 0.1 | 1.215 | 12.15 |
| 0.1 | 1.216 | 12.16 |
| 0.1 | 1.047 | 10.47 |

The antioxidant ability, related to Trolox, was calculated from two solutions having concentrations of 0.1 and 0.01 mmol/l, and it amounts: 10.54±1.02 mmol/l of the Trolox-like activity Linearity was checked in the concentration dependence; the results are given in Table 3.

Conservation of the biological activity was determined by measuring TAS in the solution in the days 0, 7 and 14. The results are given in Table 4.

TABLE 4

| Day of determination | Concentration (mmol/l) | | |
|---|---|---|---|
| | 0.01 | 0.1 | 1.0 |
| 0 | 0.531 | 1.125 | 2.374 |
| 7 | | 1.217 | |
| 14 | | 1.025 | |

Determination of the Antioxidant Ability of Fytomelanin by Means of Water-soluble Antioxidants (ACW)

For the determination solutions of the set FAT, Berlin for ACW (Antioxidant capacity in water-soluble antioxidants) were used Trolox—soluble form of vitamin E was used as a standard procedure according to instructions in the set was applied, while fytomelanin solutions with following concentrations were used for the determination:

A=1 mmol/l (5 mg/ml)
B=0.1 mmol/l (10×diluted solution A)
C=0.01 mmol/l (10×diluted solution B)

When measuring ACW, the antioxidant ability was evaluated as a shift through the "lag" phases of the curve which represents the shift of curves at the Trolox standard, from which a calibration curve was constructed which is shown in the attached figure.

The ACW concentration was calculated from the calibration curve by means of a computer. After recalculation of the ACW activity to a concentration unit of fytomelanin (0.0087:0.01) the activity which is characterised by ACW is the activity of fytomelanin=0.87 of the activity of vitamin E, if we evaluate the shift of the "lag" phase, i.e. trapping activity.

On the other hard, if we use the area of the integral of the chemiluminiscent curve for the evaluation which corresponds more to the scavenger activity this, recalculated to the unit concentration of fytomelanin, is 5.56 of the scavenger activity of Trolox.

Determination of the SOD-like Activity and $IC_{50}$ of Fytomelanin

To determine the SOD-like activity a chemiluminometric method using the chemiluminometer PHOTOCHEM was used, where the set FAT, Berlin for the SOD activity was used for the determination. The measurements were performed with the measuring time of 3 minutes, and the area integral of the chemiluminiscent curve was recorded. The value was recalculated to the unit SOD activity (by weight), and it represents 0.2 of the SOD activity. In the mole concentration recalculation to the unit activity gives the fytomelanin activity of 0.0316 of the SOD activity. The great difference is caused by a difference in the molecular weight 5000 for fytomelanin versus: 32000 for SOD.

The SOD activity is expressed by the value of $IC_{50}$ which is the substance concentration which can inhibit the detection of free radicals to 50%. After recalculation through the weight the value was 0.28 of the SOD activity.

However, if fytomelanin with increased concentration of free unpaired electrons of $10^{19}$ spin/g was used, using the above described method we achieved the following results which are displayed in Table 5.

TABLE 5

| Sample Nr. | −log $IC_{50}$ | % SOD activity |
|---|---|---|
| 1 | 6.171422 | 76.53 |
| 2 | 5.482290 | 67.98 |
| 3 | 5.768617 | 71.53 |
| 4 | 5.445406 | 67.53 |
| 5 | 5.67558 | 70.38 |
| 6 | 6.037841 | 74.87 |
| SOD | 8.064184 | 100.00 |

Influence of Fytomelanin on DNA Degradation

To determine the influence of fytomelanin on DNA degradation chromosomal bovine DNA was used, and a system xanthin-xanthin oxidase for superoxide formation.

$$X + XO \xrightarrow{2H^+} \text{uric acid} + O_2^- + H_2O$$

The reaction mixture (1 ml) contained 0.25 mg of DNAIRZ, xanthin $3,10^{-4}$ mol/l RZ. Xanthin oxidase was added to the reaction mixture so that difference delta of absorbance (510 nm) per minute which is an indicator of superoxide formation was maintained in the range of 0.03 to 0.04.

A certain volume of fytomelanin solution was added or in the control it was not added to the reaction mixture. The reaction mixture was complemented by 25 nM phosphate buffer at pH 7.4 to the volume required. The reaction mixture was incubated at 37° C. for 60 minutes. The reaction was stopped with TCA (2.8% stock solution)—75 ml. After an addition of 0.25 ml of thiobarbituric acid (TBA) the reaction mixture was heated in closed test tubes to 95° C. for 30 minutes. After cooling down it was examined by spectrophotometry against blank and using tetraethoxy propane (TEP) as a standard, formation of the final product of the oxidation damage of DNA-malondialdehyde (MDA), referred to 1 mg of DNA, was calculated. The results are given in Table 6.

TABLE 6

|  | DNA + X + XO | DNA + X + XO+ | DNA + X − XO+ | DNA + X − XO+ |
|---|---|---|---|---|
| fytomelanin mmol/l | 0.0 | 0.1 | 0.01 | 0.001 |
| MDA $\mu$mol/mg DNA | 4.87 ± 0.41 | 1.14 ± 0.12 | 2.07 ± 0.18 | 2.99 ± 0.32 |
| n | 9 | 6 | 9 | 6 |
| DNA cleavage | 100% | 23.4% | 42.5% | 61% |
| Cleavage inhibition | 0% | 76.6% | 57.5% | 39% |

Based on the achieved results it was found that:
a) fytomelanin is able to eliminate free radicals.
b) fytomelanin exhibits at least 10.00 multiple of activity of the soluble form of vitamin E (Trolox) when using organic radical ABTS from the set TAS, Randox, England.
c) fytomelanin exhibits more scavenger than trapping activity.
d) fytomelanin exhibits at least 5.50 of scavenger activity of Trolox.
e) fytomelanin exhibits at least 0.87 of trapping activity of Trolox.
f) fytomelanin exhibits at least 0.20 of activity of superoxidedismutase.
g) fytomelanin is able to inhibit DNA cleaving by superoxide. With the concentration of 0.01 mmol/l it inhibits the DNA cleaving to at least 57.5%.
h) biological activity of fytomelanin potentialises with increasing concentration of unpaired free electrons (EPR).

By basic screening tests it was further established that:
a) fytomelanin is able to block peroxidation of lipides completely.
b) fytomelanin is able to activate (anerge) leukocytes.
c) fytomelanin influences regulation and the course of the complement system.
d) fytomelanin influences contraction of blood vessels (capillaries).
e) fytomelanin keeps stable and reproducible properties for a long time, and it does not loose them even after an aggressive chemical treatment.

Industrial Applicability

Physico-chemical properties and biological activity show the possibilities of using fytomelanin in a number of industrial fields, but especially in the electronic and electrochemical industry, meat industry, agricultural industry, food production and processing, consumer chemistry and modern technologies of new materials. All over the world great attention is directed to the field of utilisation of similar materials, belonging to melanins, in nuclear technologies. A very interesting fact is utilisation of the substance, because of its pharmacological properties, in various modifications practically in all areas of cosmetics. Present tendency of application of new biotechnologies in ecological and other directions provides broad possibilities also in this field which is perspective for the next millennium.

Biological Utilisation

Starting from the present knowledge we suppose that it will be possible to use fytomelanin in the treatment of various types of malignant cancer tumours, disorders of the immune system including AIDS, diseases of blood origin and disorders following from the disturbed cell homeostasis, complex and hardly curable mental disorders (schizophrenia, epilepsy, . . . ), nervous and other regulatory systems, drug addiction. It is possible to provide a radioprotective preparation with binary effect, based on this substance.

Based on the above given facts in the literature, published so far, and based on the practical results achieved in basic screening tests we suppose that fytomelanin will be used as: antioxidant, radioprotector, phagostatic, cytostatic, anticancerogenic preparation, to treat disorders of the immune system, and the like.

What is claimed is:

1. A vegetable melanin comprising between 6 and 8 monomeric units of vegetable flavanoids wherein each monomeric unit has the chemical formula $C_{34-59}O_{14-23}H_{32-44}N_{6-8}$, wherein the molecular weight of the vegetable melanin is between $4 \times 10^3$ daltons and $6 \times 10^3$ daltons, the amount of OH groups in the vegetable melanin is from 4.02 to 4.05 percent by weight of the vegetable melanin, the amount of =O groups in the vegetable melanin is from 1.04 to 1.06 percent by weight of the vegetable melanin, the amount of carbon in the vegetable melanin is from 49.44 to 49.52 percent by weight of the vegetable melanin, the amount of hydrogen in the vegetable melanin is from 5.10 to 5.73 percent by weight of the vegetable melanin, the amount of nitrogen in the vegetable melanin is from 1.15 to 1.24 percent by weight of the vegetable melanin, the amount of oxygen in the vegetable melanin is from 41.20 to 42.10 percent by weight of the vegetable melanin, the concentration of unpaired electrons in the vegetable melanin is from $10^{18}$ to $10^{22}$ spin/g, and the infra-red spectra of the vegetable melanin exhibits absorption bands at 3433 cm$^{-1}$, 1620 cm$^{-1}$, 1400 cm$^{-1}$, and between 1200 cm$^{-1}$ and 1100 cm$^{-1}$.

2. The vegetable melanin of claim 1, wherein the monomeric units of vegetable flavanoids comprise catechins or leucoanthocyanidins.

3. A process for producing the vegetable melanin of claim 1 comprising:
    (a) obtaining vegetable raw material that comprises monomeric units of vegetable flavanoids;
    (b) extracting the vegetable raw material with a 0.05 to 0.3 M solution of an aqueous alkali metal hydroxide at a temperature between 15° C. and 75° C. to provide a basic aqueous extract;
    (c) filtering the basic aqueous extract;
    (d) adjusting the pH of the basic aqueous extract to a value of between 1 and 2 with hydrochloric acid or perchloric acid to provide an acidic aqueous extract and a precipitate of vegetable melanin;
    (e) separating the acidic aqueous extract and the precipitate of vegetable melanin; and
    (f) drying the precipitate of vegetable melanin at a temperature of between 100° C. and 110° C.

4. The process of claim 3, wherein the monomeric units of vegetable flavanoids comprise catechins or leucoanthocyanidins.

5. The process of claim 3, further comprising purifying the vegetable melanin before drying the precipitate of vegetable melanin by repeatedly washing the precipitate of vegetable melanin with a first washing solution of hydrochloric acid having a pH of between 1.0 and 3 until the first washing solution is no longer discolored by the vegetable melanin and then washing the vegetable melanin with a polar organic solvent.

6. The process of claim 5, wherein the polar organic solvent is selected from ethanol, ethyl acetate, acetone, and dimethylformamide.

7. The process of claim 5, further comprising the steps of:
   (g) dissolving the precipitate of vegetable melanin in an aqueous base to form a second aqueous basic solution;
   (h) removing solids from the second aqueous basic solution;
   (i) acidifying the second aqueous basic solution to provide a second aqueous acidic solution and a second precipitate of vegetable melanin;
   (j) separating the second precipitate of vegetable melanin from the second aqueous acidic solution;
   (k) washing the second precipitate of vegetable melanin with pharmacologically pure water;
   (l) washing the second precipitate of vegetable melanin with a second washing solution of an organic solvent while centrifuging the second precipitate of vegetable melanin until the second washing solution is no longer discolored by the second precipitate of vegetable melanin;
   (m) refluxing the second precipitate of vegetable melanin with concentrated acid;
   (n) separating the second precipitate of vegetable melanin from the concentrated acid;
   (o) washing the second precipitate of vegetable melanin with pharmacologically pure water;
   (p) washing the second precipitate of vegetable melanin with dimethylformamide; and
   (q) drying the second precipitate of vegetable melanin; wherein steps (g)–(q) are performed after the vegetable melanin is dried.

8. The method of claim 7, further comprising the steps of:
   (r) dissolving the second precipitate of vegetable melanin in an aqueous solution of ammonium hydroxide at a pH of between 10.0 and 11.0 to provide a third aqueous basic solution;
   (s) filtering the third aqueous basic solution through a membrane; and
   (t) removing the third aqueous basic solution under reduced pressure to provide a vegetable melanin that is soluble in an aqueous solution, wherein steps (r)–(t) are performed after the second precipitate of vegetable melanin is dried.

9. The process of claim 3, wherein the solution of aqueous alkali metal hydroxide, the basic aqueous extract, and the acidic aqueous extract are made with pharmacologically pure water.

10. A pharmaceutical composition comprising the vegetable melanin of claim 1 and a pharmaceutically acceptable carrier.

11. A method of blocking lipid peroxidation in a patient comprising administering to a patient in need thereof a therapeutically effective amount of the vegetable melanin of claim 1.

12. A method of activating leukocyte activity in a patient comprising administering to a patient in need thereof a therapeutically effective amount of the vegetable melanin of claim 1.

13. A method of regulating the complement system in a patient comprising administering to a patient in need thereof a therapeutically effective amount of the vegetable melanin of claim 1.

14. A method of contracting blood vessels in a patient comprising administering to a patient in need thereof a therapeutically effective amount of the vegetable melanin of claim 1.

15. A vegetable melanin comprising between 6 and 8 monomeric units of vegetable flavanoids wherein each monomeric unit has the chemical formula $C_{34-59}O_{14-23}H_{32-44}N_{6-8}$, wherein the molecular weight of the vegetable melanin is between $4 \times 10^3$ daltons and $6 \times 10^3$ daltons, the amount of carbon in the vegetable melanin is from 49.44 to 49.52 percent by weight of the vegetable melanin, the amount of hydrogen in the vegetable melanin is from 5.10 to 5.73 percent by weight of the vegetable melanin, the amount of nitrogen in the vegetable melanin is from 1.15 to 1.24 percent by weight of the vegetable melanin, the amount of oxygen in the vegetable melanin is from 41.20 to 42.10 percent by weight of the vegetable melanin.

* * * * *